(12) United States Patent
Franke et al.

(10) Patent No.: US 12,076,539 B2
(45) Date of Patent: Sep. 3, 2024

(54) INJECTOR DEVICE

(71) Applicant: SANOFI, Paris (FR)

(72) Inventors: Beate Franke, Frankfurt am Main (DE); Sean Phillips, Bridgewater, NJ (US); Edward Liscio, Bridgewater, NJ (US); Nie Weiyan, Bridgewater, NJ (US); Marc Anderson, Bridgewater, NJ (US); Tim Glässer, Rüsselsheim (DE); Matthias Rau, Rüsselsheim (DE)

(73) Assignee: Sanofi, Paris (FR)

( * ) Notice: Subject to any disclaimer, the term of this patent is extended or adjusted under 35 U.S.C. 154(b) by 1058 days.

(21) Appl. No.: 16/968,957

(22) PCT Filed: Feb. 8, 2019

(86) PCT No.: PCT/EP2019/053085
§ 371 (c)(1),
(2) Date: Aug. 11, 2020

(87) PCT Pub. No.: WO2019/154960
PCT Pub. Date: Aug. 15, 2019

(65) Prior Publication Data
US 2020/0397999 A1    Dec. 24, 2020

(30) Foreign Application Priority Data
Feb. 12, 2018  (EP) .................................. 18305143

(51) Int. Cl.
*A61M 5/315* (2006.01)
*A61M 5/20* (2006.01)
(Continued)

(52) U.S. Cl.
CPC ...... *A61M 5/31571* (2013.01); *A61M 5/2033* (2013.01); *A61M 5/3204* (2013.01); *A61M 2005/208* (2013.01); *A61M 5/2466* (2013.01)

(58) Field of Classification Search
CPC ............ A61M 5/31571; A61M 5/2033; A61M 5/3204; A61M 5/2466; A61M 2005/208;
(Continued)

(56) References Cited

U.S. PATENT DOCUMENTS

| 3,136,313 A | 6/1964 | Gosta et al. |
| 2006/0167412 A1 | 7/2006 | Marshall |

(Continued)

FOREIGN PATENT DOCUMENTS

| CN | 105246528 | 1/2016 |
| JP | 2016-519976 | 7/2016 |

(Continued)

OTHER PUBLICATIONS

PCT International Preliminary Report on Patentability in International Appln. No. PCT/EP2019/053085, dated Aug. 18, 2020, 9 pages.
PCT International Search Report and Written Opinion in International Appln. No. PCT/EP2019/053085, dated Apr. 12, 2019, 12 pages.

*Primary Examiner* — Theodore J Stigell
(74) *Attorney, Agent, or Firm* — Fish & Richardson P.C.

(57) ABSTRACT

An injector device is configurable between a safe state and an operable state and comprises a housing having a distal end and a proximal end; a medicament cartridge disposed within the housing; a needle unit comprising a needle and being disposed in the distal end of the housing; a sleeve displaceable along a longitudinal axis of the device between a first position in which the sleeve conceals the needle and a second position in which the needle is exposed from an end of the sleeve; a locking mechanism configured to prevent displacement of the sleeve when the device is in the safe state; and a button disposed in the proximal end of the housing, the button being configured to switch the device between the safe state and the operable state by releasing the (Continued)

locking mechanism when the button is pressed from an initial position into a depressed position during use.

16 Claims, 7 Drawing Sheets

(51) Int. Cl.
*A61M 5/32* (2006.01)
*A61M 5/24* (2006.01)

(58) Field of Classification Search
CPC .... A61M 2005/2013; A61M 2005/247; A61M 2005/3267
See application file for complete search history.

(56) References Cited

U.S. PATENT DOCUMENTS

| | | |
|---|---|---|
| 2013/0237921 A1 | 9/2013 | Lannan et al. |
| 2013/0317479 A1 | 11/2013 | Brereton et al. |
| 2015/0231333 A1 | 8/2015 | Lannan et al. |
| 2016/0008541 A1 | 1/2016 | Hirschel et al. |
| 2016/0106920 A1* | 4/2016 | Stefansen ............ A61M 5/2033 |
| 2017/0021103 A1 | 1/2017 | Mosebach et al. |

FOREIGN PATENT DOCUMENTS

| | | |
|---|---|---|
| WO | WO 2014/057286 | 4/2014 |
| WO | WO 2014/195183 | 12/2014 |
| WO | WO 2018/015238 A1 | 1/2018 |

* cited by examiner

INJECTOR DEVICE

CROSS REFERENCE TO RELATED APPLICATIONS

The present application is the national stage entry of International Patent Application No. PCT/EP2019/053085, filed on Feb. 8, 2019, and claims priority to Application No. EP 18305143.2, filed on Feb. 12, 2018, the disclosures of which are incorporated herein by reference.

TECHNICAL FIELD

The present disclosure relates to an injector device for a medicament.

BACKGROUND

Cartridge injection devices, for example cartridge auto-injectors, typically have a sleeve which conceals a needle for subcutaneous medicament delivery into a patient. The sleeve is usually displaced along a longitudinal axis of the device to expose the needle either during or prior to injection.

SUMMARY

It is an object of the present disclosure to provide an injector device configurable between a safe state and an operable state comprising:
- a housing having a distal end and a proximal end;
- a medicament cartridge disposed within the housing;
- a needle unit comprising a needle, the needle unit being disposed in the distal end of the housing;
- a sleeve displaceable along a longitudinal axis of the device between a first position in which the sleeve conceals the needle and a second position in which the needle is exposed from an end of the sleeve;
- a locking mechanism which prevents displacement of the sleeve when the device is in the safe state; and
- a button disposed in the proximal end of the housing, the button being configured to switch the device between the safe state and the operable state by releasing the locking mechanism to allow displacement of the sleeve when, in use, the button is pressed from an initial position into a depressed position.

Therefore the sleeve is secured to prevent exposure of the needle prior to movement of the button into the depressed position. This prevents premature exposure of the needle and accidental injury.

The injector may further comprise a plunger displaceable to drive medicament from the cartridge through the needle; and a plunger mechanism triggerable to displace the plunger during operation of the device.

Therefore the plunger can be mechanically, rather than manually, operated to ensure consistent delivery characteristics.

With the injector device in the safe state, the cartridge may be spaced from the needle unit, wherein the button is configured to move the cartridge onto the needle unit to fluidly connect the needle with the cartridge when, in use, the button is pressed from the initial position to the depressed position.

Therefore, prior to use of the device, the needle unit and needle are spaced from the cartridge. This has the advantage that the cartridge remains sealed up until the time that the device is required for use.

The sleeve may be configured to trigger the plunger mechanism when, during use, the sleeve is moved from the first position to the second position.

Therefore medicament is automatically delivered during injection.

The plunger mechanism may comprise: a coil spring which, when the plunger mechanism is triggered, provides a force to displace the plunger; and a spring retaining mechanism which prevents premature displacement of the plunger prior to the plunger mechanism being triggered.

The spring retaining mechanism may comprise a coupling and a retaining pin; the coupling being arranged to couple the spring to the retaining pin, prior to the plunger mechanism being triggered.

The coupling may comprise a slot which cooperates with the retaining pin.

The retaining pin may be held in cooperation with the slot by the sleeve and wherein axial movement of the sleeve between the first position and the second position aligns the retaining pin with an opening in the sleeve such that the retaining pin is displaceable out of the slot.

The retaining pin may extend from a cantilever spring arm which is configured to bias the retaining pin out of the slot.

Contacting surfaces of the slot and the retaining pin may be arranged such that the retaining pin is displaceable out of the slot by axial movement of the coupling.

Therefore the plunger mechanism is simply operated so that medicament is automatically delivered during injection.

The locking mechanism may comprise a hook that depends from a wall of the device and wherein the hook abuts the sleeve to prevent the sleeve moving relative to the housing when the button is in the initial position.

The button may be configured to act on the hook, when during use, it is moved from the initial position to the depressed position, to displace the hook out of abutting relation with the sleeve.

The injector device may further comprise a reservoir of medicament in the medicament cartridge.

These and other aspects of the disclosure will be apparent from and elucidated with reference to the embodiments described hereinafter.

BRIEF DESCRIPTION OF FIGURES

Embodiments of the disclosure will now be described, by way of example only, with reference to the accompanying drawings, in which.

DETAILED DESCRIPTION

Figure 1A:
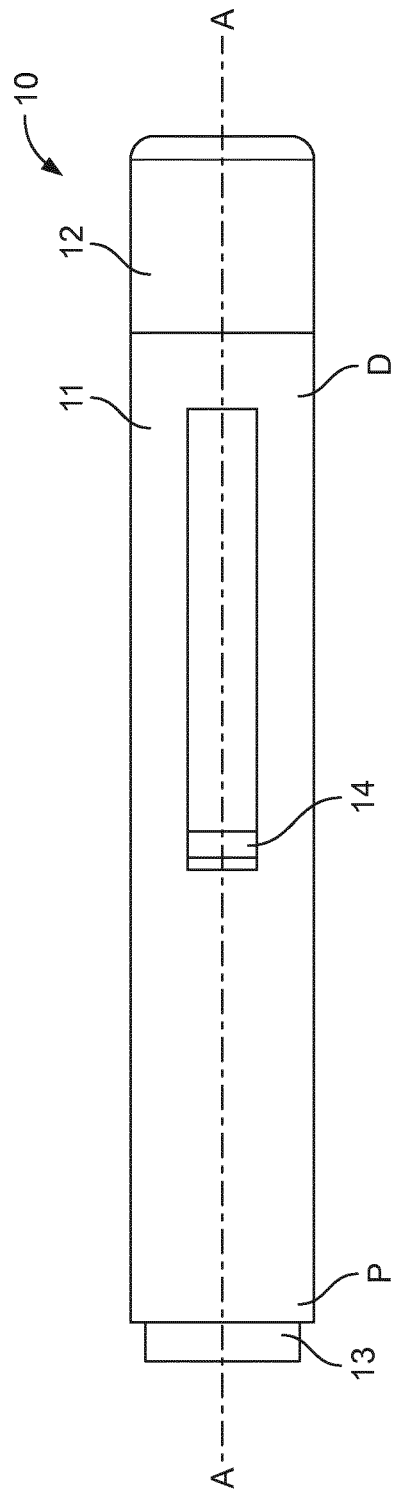
FIG. 1A is a schematic side view of an injector device and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
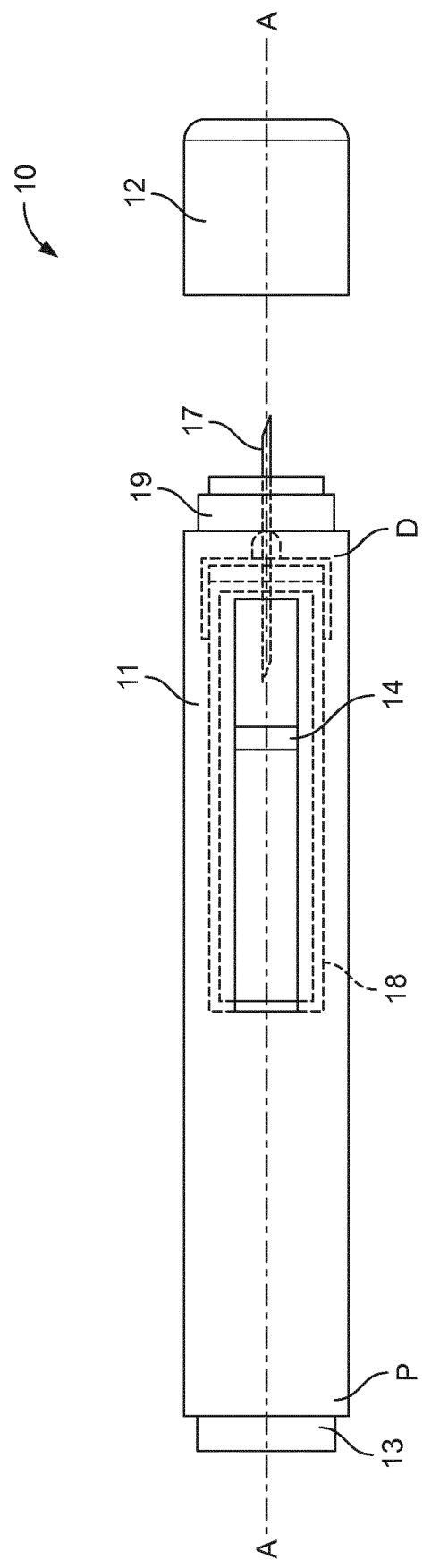
FIG. 1B is a schematic side view of the injector device of FIG. 1A, with the cap removed from the housing.

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Figure 2A:
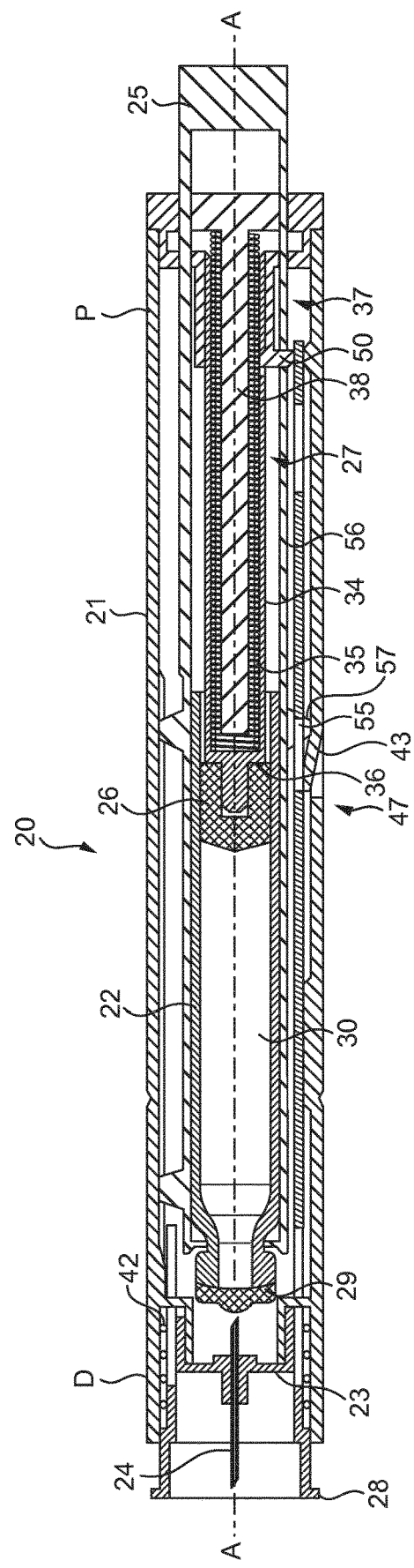
FIG. 2A shows a section view of an injector device.
Figure 2B:
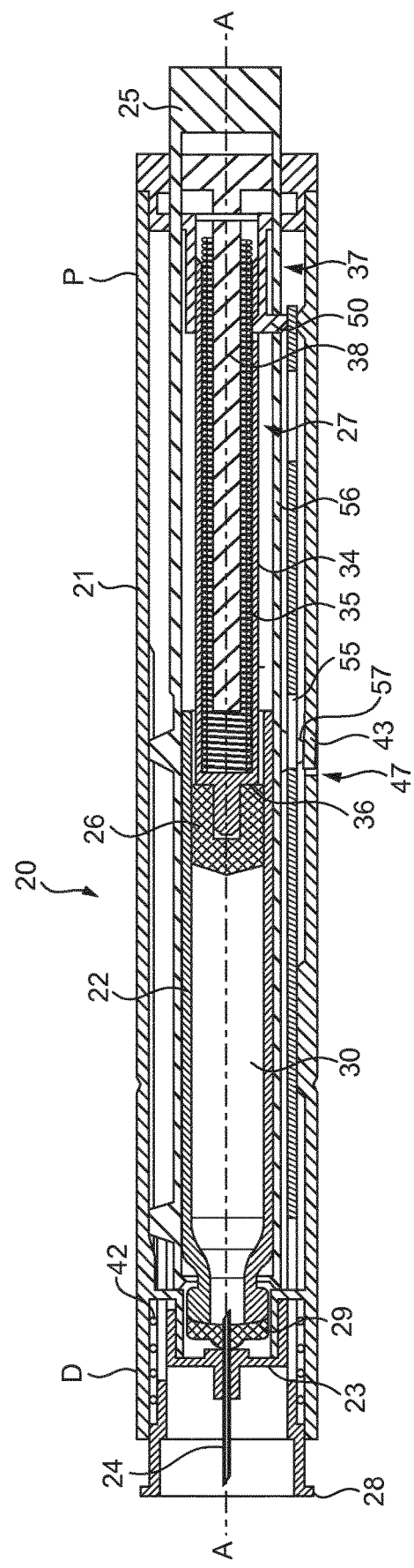
FIG. 2B shows a section view of the injector device.
Figure 2C:
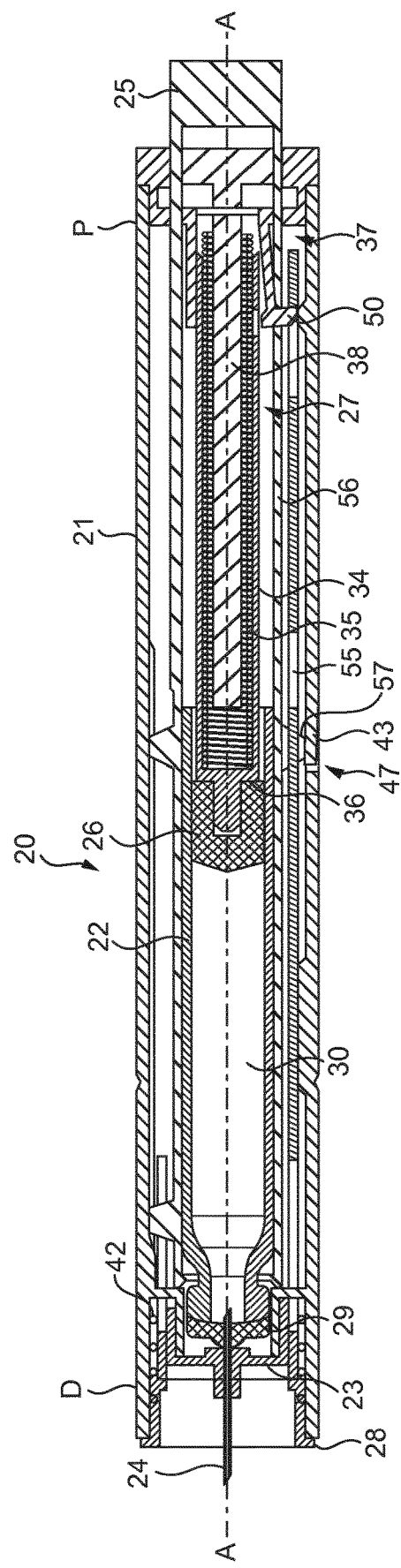
FIG. 2C shows a section view of the injector device.

FIGS. 2A to 2C show another injector device 20. The injector device 20 is configurable between a safe state and an operable state and comprises: an elongate housing 21 having a distal end D and a proximal end P; a medicament cartridge 22 disposed within the housing 21; a needle unit 23 comprising a needle 24, the needle unit 23 being disposed in the distal end D of the housing 21; and a button 25 disposed in the proximal end P of the housing 21.

The device further comprises a sleeve 28 which is displaceable along the longitudinal axis A-A of the device 20 between a first position in which the sleeve 28 conceals the needle 24, as illustrated in FIG. 2A, and a second position in which the needle 24 is exposed from an end of the sleeve 28, as shown in FIG. 2C.

The sleeve 28 slides telescopically with respect to the housing 21 and is biased into the first position by a spring 42. The spring 42 is disposed between the sleeve 28 and an inner surface of the housing 21 so that it is concealed during use of the device 20. A locking mechanism 47 is provided to prevent displacement of the sleeve 28 when the device is in the safe state.

The button 25 is configured to switch the device from the safe state into the operable state by releasing the locking mechanism 47 to allow displacement of the sleeve 28, when, in use, the button 25 is pressed from an initial position into a depressed position.

The button 25 is further configured to move the cartridge 22 onto the needle unit 23 to fluidly connect the needle 24 with the cartridge 22 as it is pressed into the depressed position. FIG. 2B shows the button 25 in the depressed position.

The cartridge 22 has a distal end sealed by a foil cap or rubber bung 29, which is adjacent the needle unit 23, and a proximal end sealed by a plunger 26. A middle of the needle 24 is gripped by the needle unit 23, which itself is fixed in place relative to the housing 21 so that, during use, when the button 25 is depressed a proximal end of the needle 24 penetrates the foil or rubber seal 29 to communicate with a reservoir of medicament 30 provided in the cartridge 22.

The device further comprises a plunger mechanism 27 triggerable to displace the plunger 26 during operation of the device 20 and drive medicament 30 from the cartridge 22. The plunger mechanism 27 is disposed between the button 25 and the cartridge 22 and comprises a spring 35, in this case a coil spring, which, when the plunger mechanism 27 is triggered, is displaced along the longitudinal axis A-A of the device to displace the plunger 26 and drive medicament 30 from the cartridge 22. The plunger mechanism 27 also comprises a spring retaining mechanism 37 comprising a coupling 34 and a retaining pin 50. The spring retaining mechanism 37 is configured to prevent displacement of the plunger 26 before the plunger mechanism 27 is triggered; in which condition, the coupling 34 connects the spring 35 to the retaining pin 50 to retain the spring 35 and prevent it displacing the plunger 26.

In the illustrated example, the coupling 34 consists of a tubular shaft 34 having a closed distal end 36 which faces the plunger 26. The spring 35 is received within the shaft 34 with a distal end of the spring 35 abutted against the closed distal end 36 of the shaft 34 and a proximal end of the spring 35 abutted against an internal surface of the housing 21. When the plunger mechanism 27 is triggered, the spring 35 is released from a coiled position and reacts against the internal surface of the housing 21 and the closed end 36 of the shaft 34 to displace the shaft 34 and the plunger 26. The mechanism 27 may further be provided with a centring pin 38 which locates within the coil spring 35 to keep it aligned to the longitudinal axis A-A as it extends from the hollow portion of the shaft 34.

The retaining pin 50 is moveable between a first position, in which the retaining pin 50 is configured to retain the spring 35 in the coiled position, and a second position, in which the retaining pin 50 is displaced to release the spring 35. In the first position—as most clearly illustrated by FIG. 3—the retaining pin 50 cooperates with a slot 51 in the shaft 34 to fix the shaft 34 in an axial direction relative to the housing 21, via an arm 52, which attaches the retaining the pin 50 to the housing 21.

The arm 52 is cantilevered from an internal surface of the housing 21 and is readily deformable so that the retaining pin 50 may be displaced out of cooperation with the slot 51 in the shaft 34 when the arm 52 is bent along its length. The arm 52 may be resiliently deformable so that it is inherently biased into the second position or, alternatively, the abutting surfaces of the retaining pin 50 and the slot 51 in the shaft 34 may be inclined so that the axial force generated by the spring 35 has a component that acts outward on the retaining pin 50, that is a component that acts transverse to the axis A-A of the device.

In either case, the retaining pin 50 is held in the first position by a portion 53 of the sleeve 28. Specifically, the portion 53 of the sleeve 28 abuts a rear end of the pin 50 which prevents it being displaced out of the slot 51 in the shaft 34 when the sleeve 28 is in the first position. An opening 54 adjacent said portion 53 of the sleeve 28 is aligned with the retaining pin 50 when the sleeve 28 is moved to the second position so that the pin 50 is displaceable out of the slot 51 in the shaft 34 and into the opening 54 in the sleeve 28. In this way, movement of the sleeve 28 from the first position to the second position triggers the plunger mechanism 27.

During use of the device, the button 25 is pressed into the depressed position to engage the needle unit 23 and cartridge 22 and release the locking mechanism 27. The device is then in the operable state in which the sleeve 28 is displaceable relative to the housing 21. The user can therefore press the distal end D of the device up against an injection site to displace the needle shield 28 and expose the needle 24. This causes penetration of the injection site with the needle 24. After a predetermined insertion distance of the needle 24 into a subcutaneous region of the injection site, the opening 54 in the sleeve is aligned with the retaining pin 50, thereby triggering injection as described above.

Figure 4:
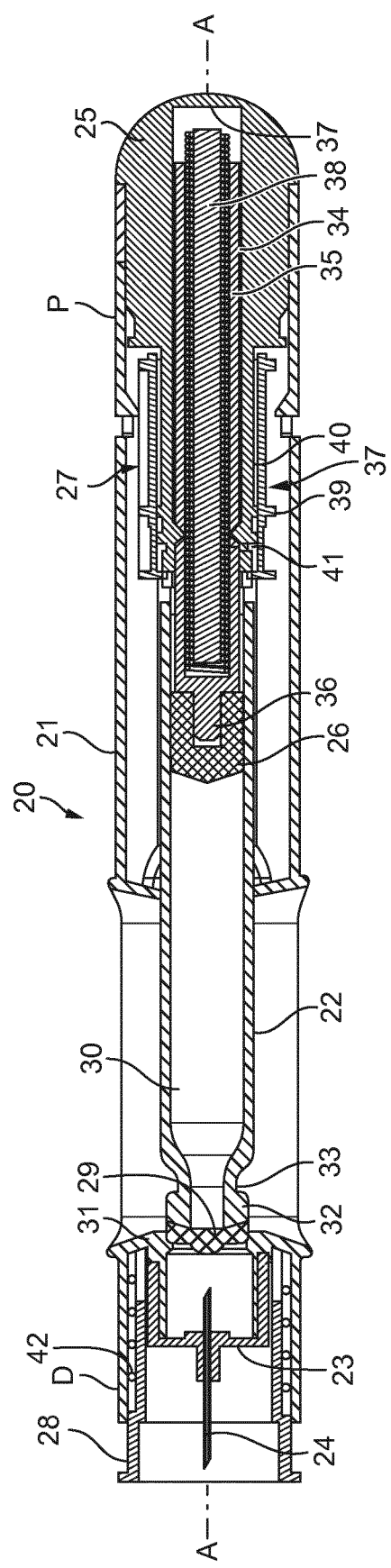
FIG. 4 shows a section view of an injector device.

Another injector device is shown in FIG. 4, in which like features retain the same reference numbers. On this device, the spring retaining mechanism 37 instead comprises a collar 39, the collar 39 being rotatable about the longitudinal axis A-A between a locked position, in which the spring 35 is locked in place, and an unlocked position, in which the spring 35 is free to displace the plunger 26.

The spring retaining mechanism further comprises locking arms 40 which cooperate with the collar 39 to hold the shaft 34 against the force of the spring 35, prior to operation of the device 20. The locking arms 40 are integral with the button 25 and extend therefrom into the housing 21. Ends of the arms 40 are provided with a protrusion 41 that each extend through a corresponding opening in the shaft 34 to prevent the shaft 34 moving in the axial direction independently of the button 25. In this way, the shaft 34 and plunger mechanism 27 are coupled to the button 25 when the collar is in the locked position.

The arms are inherently biased away from the shaft 34 but, with the collar 39 in the locked position, are held against the shaft 34 by the collar 39. Rotation of the collar 39 into the unlocked position aligns slots in the collar 39 with each of the locking arms 40 so that they spring outwards through said slots and away from the longitudinal axis A-A. This action disengages the protrusions 41 from the holes in the shaft 34, thus allowing the spring 35 to displace the plunger 26.

The plunger mechanism 27 is coupled to the button 25 by the locking arms, as described above, so that when the button 25 is depressed from the first position to the depressed position, the plunger mechanism 27 moves from an initial position, in which the plunger mechanism 27 is initially spaced from the sleeve 28, into a primed position in which the collar 39 of the plunger mechanism 27 abuts the sleeve 28.

Specifically, a follower surface of the collar 39 abuts a distal edge (not shown) of the sleeve 28, which distal edge is inclined relative to a direction perpendicular to the longitudinal axis A-A, so that, during axial displacement of the sleeve 28, the collar 39 is rotated by said inclined edge about the axis A-A from the locked position into the unlocked position.

During use, the button 25 is pressed into the depressed position to move the plunger mechanism 27 into the primed position and engage the needle unit 23 and cartridge 22; subsequently the distal end D of the device 20 is pressed up against an injection site of the user, displacing the needle shield 28 and causing the needle 24 to penetrate the user's skin, whereupon the displaced needle shield 28 triggers the plunger mechanism 27 and starts the injection event.

In this example, a restraint element 31 extends from an internal wall of the housing 21 adjacent the needle holder 23 to provide haptic feedback as the cartridge 22 engages the needle unit 23. The restraint element may consist of a lip 31, as shown, which extends internally from the housing 21 toward the longitudinal axis A-A and into the path of the cartridge 22. The lip 31 has a degree resilient deformability so that when the user operates the button 25, the cartridge 22 pushes past the lip 31 which resists in a manner that is discernible to the user to signify that the cartridge 22 and the needle unit 23 have combined. With the button 25 in the depressed position, the lip 31 locates in a neck 33 of the cartridge to secure the cartridge 22 in the needle unit 23.

Figure 5:
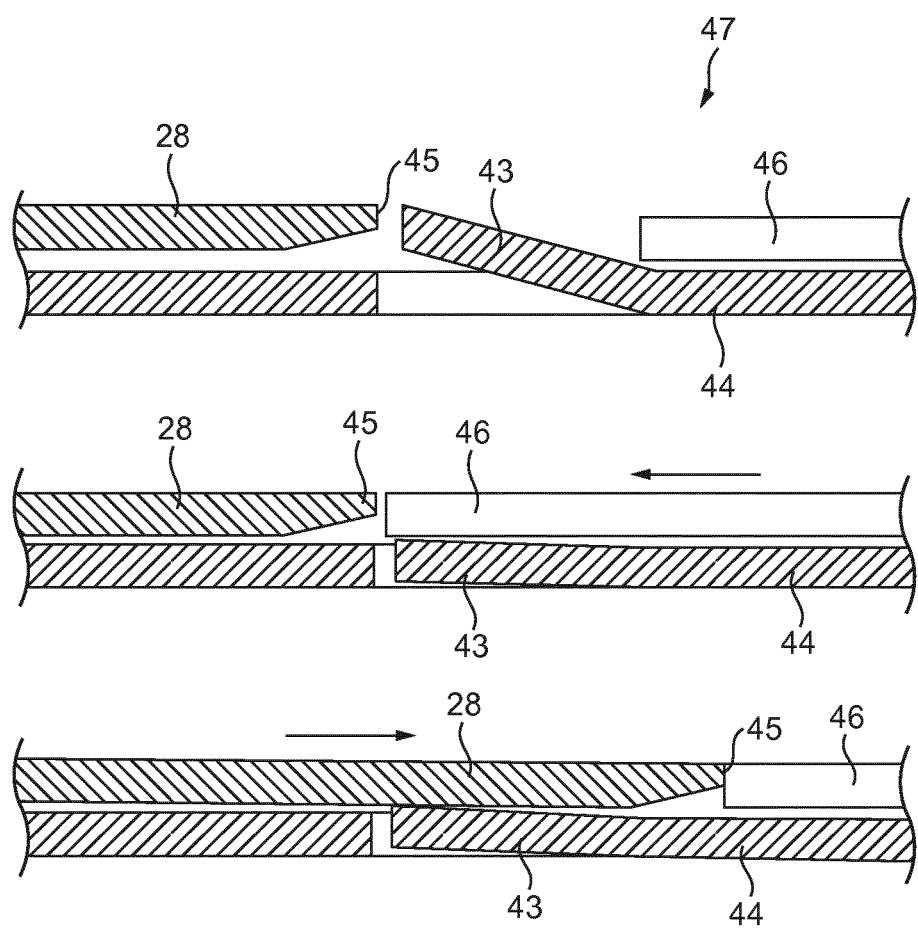
FIG. 5 shows a detail section view of the injector device.

The particular arrangement of the locking mechanism 47 of the device illustrated by FIG. 4 is shown in detail in FIG. 5. As illustrated, the locking mechanism comprises a hook 43 that depends from a wall 44 of the device 20. In particular, the hook 43 may be a portion of wall 44 that is bent away from an inner face of the housing 21 toward the longitudinal axis A-A to obstruct the distal edge 45 of the sleeve 28, when the device is in the safe state. In such an example the button 25 will be provided with a releasing means 46. In the illustrated example the releasing means 46 is an arm 46 which is integrally formed with the button 25 and extends into the housing 21. The arm 46 is configured to slide over the hook 43 to displace it outwards as the button 25 is moved from the first position to the depressed position, thereby allowing free movement of the sleeve 28.

In another unillustrated example, the hook may abut the collar 39 to prevent rotation of the collar 39 when the button 25 is in the initial position, thereby preventing the plunger mechanism 27 being triggered before the cartridge 22 has engaged the needle unit 23.

Figure 3:
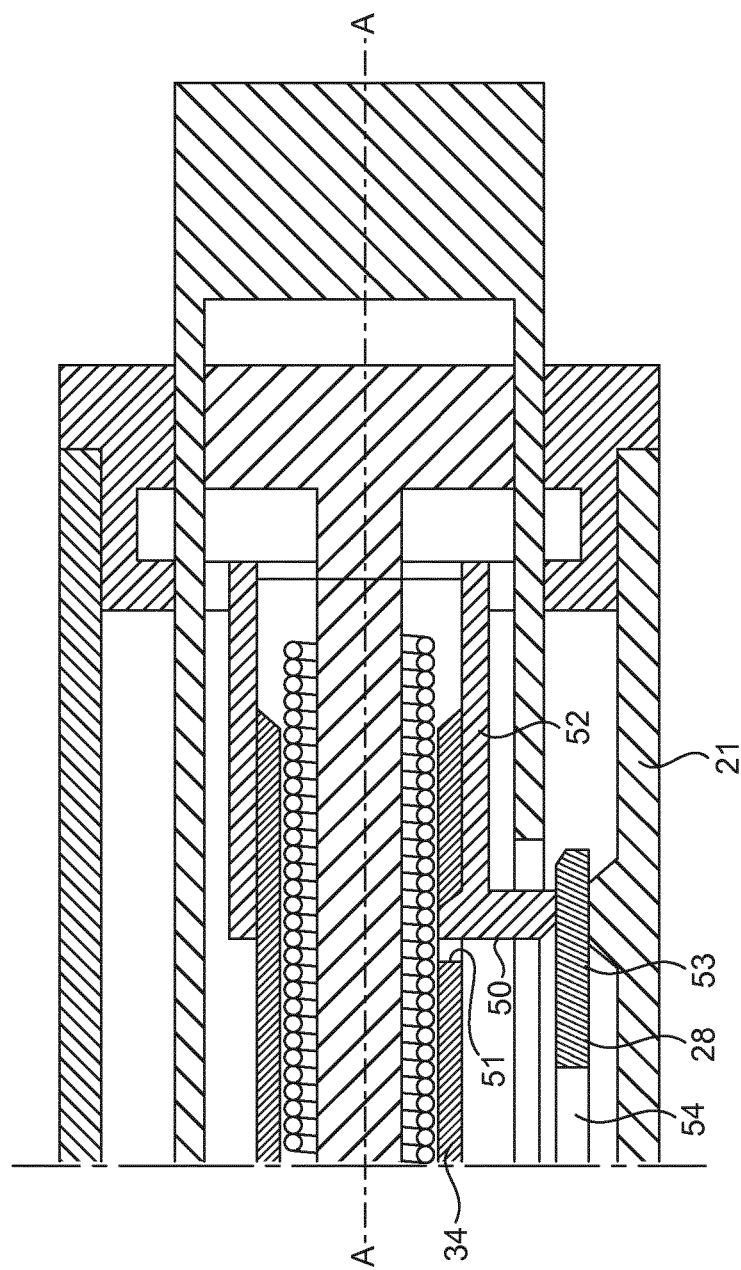
FIG. 3 shows a detail section view of the injector device.

Referring again to the example illustrated by FIGS. 2A to 3, the locking mechanism 47 again comprises a hook 43 which extends toward the longitudinal axis A-A when the device is in the safe state. In this example, the hook 43 obstructs a second opening 55 in the sleeve 28. The hook 43 is displaced outwards of the longitudinal axis A-A and out of the second opening 55 of the sleeve 28 as the button 25 is pressed into the depressed position in use. Specifically, an arm 56 extends from the button 25, into the device and into contact with a proximal end of the cartridge 22 so that the cartridge 22 and button 25 move together, the button 25 being pressable by an amount necessary to engage the cartridge 22 with the needle unit 23. A protrusion 57 is provided on the arm 56 which interacts with the hook 43 as the button 25 is pressed, displacing it outward to allow movement of the sleeve 28.

The injector device may further comprise a reservoir of medicament in the medicament cartridge.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injector device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injector devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful for the present invention disclosure, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

The invention claimed is:

1. An injector device configurable between a safe state and an operable state, the injector device comprising:
   a housing having a distal end and a proximal end;
   a medicament cartridge disposed within the housing;
   a needle unit comprising a needle, the needle unit being disposed in the distal end of the housing;
   a sleeve displaceable along a longitudinal axis of the injector device between a first position in which the sleeve conceals the needle and a second position in which the needle is exposed from an end of the sleeve;
   a locking mechanism that prevents displacement of the sleeve when the injector device is in the safe state; and
   a button disposed in the proximal end of the housing, the button being configured to switch the injector device between the safe state and the operable state by releasing the locking mechanism to allow displacement of the sleeve when the button is pressed from an initial position into a depressed position during use.

2. An injector device according to claim 1, further comprising:
   a plunger displaceable to drive medicament from the medicament cartridge through the needle; and
   a plunger mechanism triggerable to displace the plunger during operation of the injector device.

3. An injector device according to claim 2, wherein the sleeve is configured to trigger the plunger mechanism when the sleeve is moved from the first position to the second position during use.

4. An injector device according to claim 3, wherein the plunger mechanism comprises:
   a coil spring that provides a force to displace the plunger when the plunger mechanism is triggered; and
   a spring retaining mechanism that prevents premature displacement of the plunger prior to the plunger mechanism being triggered.

5. An injector device according to claim 4, wherein the spring retaining mechanism comprises a coupling and a retaining pin, the coupling being arranged to couple the spring to the retaining pin prior to the plunger mechanism being triggered.

6. An injector device according to claim 5, wherein the coupling comprises a slot that cooperates with the retaining pin.

7. An injector device according to claim 6, wherein the retaining pin is held in cooperation with the slot by the sleeve, and wherein axial movement of the sleeve between the first position and the second position aligns the retaining pin with an opening in the sleeve such that the retaining pin is displaceable out of the slot.

8. An injector device according to claim 7, wherein the retaining pin extends from a cantilever spring arm.

9. An injector device according to claim 8, wherein the cantilever spring arm is configured to bias the retaining pin out of the slot.

10. An injector device according to claim 7, wherein contacting surfaces of the slot and the retaining pin are arranged such that the retaining pin is displaceable out of the slot by axial movement of the coupling.

11. An injector device according to claim 1, wherein in the safe state, the medicament cartridge is spaced from the needle unit.

12. An injector device according to claim 11, wherein the button is configured to move the medicament cartridge onto the needle unit to fluidly connect the needle with the medicament cartridge when the button is pressed from the initial position to the depressed position during use.

13. An injector device according to claim 1, wherein the locking mechanism comprises a hook that depends from a wall of the injector device.

14. An injector device according to claim 13, wherein the hook abuts the sleeve to prevent the sleeve from moving relative to the housing when the button is in the initial position.

15. An injector device according to claim 14, wherein the button is configured to act on the hook when the button is moved from the initial position to the depressed position to displace the hook out of abutting relation with the sleeve.

16. An injector device according to claim 1, further comprising a reservoir of medicament in the medicament cartridge.

* * * * *